United States Patent [19]
Giordano et al.

[11] Patent Number: 4,937,379
[45] Date of Patent: Jun. 26, 1990

[54] CARBOXYLIC ACID SYNTHESIS PROCESS

[75] Inventors: Claudio Giordano, Vicenza; Marco Villa, Milan, both of Italy

[73] Assignee: Zambon S.p.A., Vicenza, Italy

[21] Appl. No.: 79,426

[22] Filed: Jul. 30, 1987

[30] Foreign Application Priority Data

Aug. 1, 1986 [IT] Italy ................. 21359 A/86

[51] Int. Cl.$^5$ ............................................. C07C 63/04
[52] U.S. Cl. .................................. 562/493; 562/490; 562/465; 562/466; 562/472
[58] Field of Search ............... 562/493, 490, 465, 466, 562/472

[56] References Cited
U.S. PATENT DOCUMENTS 4,433,160 2/1984 Amano et al. ................. 562/493

*Primary Examiner*—Paul J. Killos
*Attorney, Agent, or Firm*—Cushman, Darby and Cushman

[57] ABSTRACT

A process is described for preparing alpha-arylalkanoic acids, which comprises preparing and subsequently rearranging ketals of formula

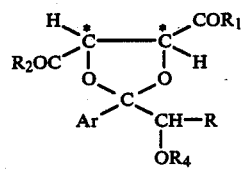

(II)

(in which Ar, R, $R_1$, $R_2$ and $R_4$ have the meanings given in the description).

The ketals of formula II are prepared from the corresponding alpha-hydroxyketals.

The rearrangement reaction is conducted under mild conditions.

11 Claims, No Drawings

CARBOXYLIC ACID SYNTHESIS PROCESS

This invention relates to a process for the synthesis of alpha-arylalkanoic acids and in particular a process for the preparation of compounds of formula $$\text{Ar}-\underset{\underset{R}{|}}{\text{CH}}-\text{COOH} \qquad (I)$$

where R represents a $C_1$–$C_4$ alkyl and Ar represents an aryl group such as phenyl, diphenyl or naphthyl, possibly substituted with one or more groups chosen from $C_1$–$C_4$ alkyls, hydroxyls, halogens, alkoxys and haloalkoxys having 1–4 carbon atoms.

The compounds of formula I comprise numerous anti-inflammatory medicaments such as ibuprofen [2-(4-isobutylphenyl)-propionic acid], naproxen [S(+)-2-(6-methoxy-2-naphthyl)-propionic acid], flurbiprofen [2-(2-fluoro-4-diphenyl)-propionic acid] and their precursors, or can constitute intermediates useful in the preparation of pyrethroid insecticides.

The compounds of formula I possess at least one centre of asymmetry, namely the alpha carbon atom of the carboxyl, and according to the process of the present invention can be obtained either in raceme mixture or in optically active form.

This process comprises the preparation and rearrangement of cyclic ketals of formula $$\text{(II)}$$

where R and Ar have the aforesaid meanings; $R_1$ and $R_2$ can be the same or different and represent an $OR_3$ group in which $R_3$ represents a hydrogen atom, a $C_1$–$C_6$ alkyl, a $C_3$–$C_6$ cycloalkyl, a phenyl or benzyl, or an amino, monoalkylamino or dialkylamino group; $R_4$ represents a $POCl_2$, $PCl_2$, $POBr_2$, $PBr_2$, $SeOBr$ group, an $SOX$ or $SO_2X$ group in which X represents a chlorine, fluorine or bromine atom, a trifluoromethyl group or an $OR_5$ group in which $R_5$ represents a $C_1$–$C_6$ alkyl, a phenyl or a tolyl; the carbon atoms marked with an asterisk both simultaneously have R or S configuration.

The ketals of formula II are new, and form a further subject of the invention; they are prepared from the corresponding alpha-hydroxy derivatives of formula $$\text{(V)}$$

(where Ar, R, $R_1$ and $R_2$ have the aforesaid meanings), described in European patent application No. 158255 (Zambon S.p.A.).

These alpha-hydroxyketals have a further centre of asymmetry on the carbon atom bonded to the hydroxyl group, and thus exist as epimers.

In the aforesaid European patent application, the compounds of formula V are described both as single epimers and as their mixtures.

The alpha-hydroxyketals (V) are reacted, possibly in the presence of a base, with a compound of formula $$R_4 X_1 \qquad (IV)$$

(where $R_4$ has the aforesaid meanings and $X_1$ represents a chlorine or bromine atom), or with sulphur dioxide and halogen, in particular chlorine.

The compounds of formula IV can be thionyl chloride, thionyl bromide, sulphuryl chloride, sulphuryl fluoride, trifluoromethanesulphonylchloride, selenyl bromide, selenyl chloride, phosphoryl chloride, phosphoryl bromide, phosphorus trichloride, phosphorus tribromide, methoxysulphonylchloride, methoxysulphinylchloride, phenoxysulphonylchloride, phenoxysulphinylchloride, or sulphuryl chloride ($SO_2ClF$).

The ketals of formula II are rearranged under mild conditions to obtain esters of formula $$\text{Ar}-\underset{\underset{R}{|}}{\overset{*}{\text{CH}}}-\text{COO}-\underset{\underset{COR_2}{|}}{\overset{*}{\text{CH}}}-\underset{\underset{COR_1}{|}}{\text{CH}}-\text{OH} \qquad (III)$$

(where Ar, R, $R_1$ and $R_2$ have the aforesaid meanings), described in European patent application No. 158225, which also describes their hydrolysis to obtain compounds of formula I.

Esters different from those of formula III can be obtained, depending on the conditions of the rearrangement reaction.

A process which in some aspects is similar to that of the present invention but which is performed on different ketals is described in European patent application No. 160241 (Kyowa Hakko Kogyo Co., Ltd.). If applied to the ketals of formula V this process does not give the desired results.

A practical embodiment of the invention is as follows: The derivatives of formula II are obtained from the corresponding alpha-hydroxyketals V by reaction with the compounds IV or with sulphur dioxide and halogen, in particular chlorine.

In this reaction, the compounds IV are used in excess with respect to the alpha-hydroxyketal, in a ratio of between 1:1.5 and 1:3.

This reaction is effected at a temperature of between −60° and 100° C. for a time of some hours in organic solvents, possibly in the presence of a base.

Suitable bases, which are used in a ratio preferably of between 1:1.5 and 1:3 with respect to the alpha-hydroxyketal, are aliphatic or aromatic primary, secondary or tertiary amines, and in particular pyridine, triethylamine and isopropylamine.

Suitable solvents are amides such as dimethylformamide, dimethylacetamide, hexamethylphosphorous triamide, ureas such as tetramethylurea, and thioamides such as dimethylthioformamide, or their mixtures with inert organic solvents such as tetrahydrofuran or dichloromethane.

By using the aforesaid aprotic dipolar solvent, the use of a base can be avoided.

The rearrangement reaction is conducted on the compounds of formula II using protic solvents such as lower alcohols, possibly in mixture with water, or dipolar aprotic solvents such as dimethylformamide, in a time of between 1 and 3 hours at a temperature of between ambient and the reflux temperature.

Subsequent preferably acid hydrolysis of the esters (III) which are obtained after rearrangement leads to the formation of the desired alpha-arylalkanoic acids (I).

A particular aspect of the process according to the present invention is the preparation of ketals of formula

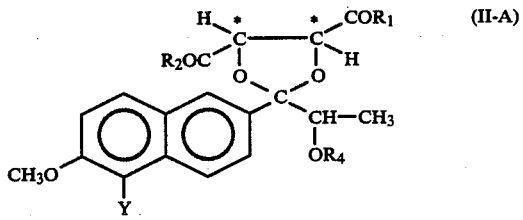

where $R_1$, $R_2$ and $R_4$ have the aforesaid meanings and Y represents a hydrogen atom or halogen atom, in particular chlorine or bromine.

These compounds, as in the case of the derivatives of formula II, are obtained from the corresponding alpha-hydroxyketals by reaction with a compound of formula IV or with sulphur dioxide and halogen.

If Y is hydrogen, this reaction can often lead to halogenation of the naphthyl in position 5. If necessary, the halogen can be eliminated from any subsequent intermediate in the synthesis, or from the final product.

By rearrangement and hydrolysis, the compounds II-A alpha-arylalkanoic acids of formula

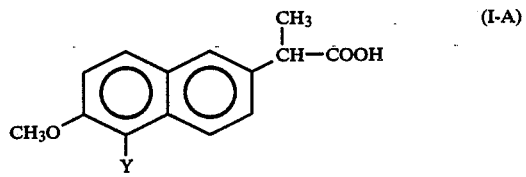

A further particular aspect of the process according to the present invention is the preparation of optically active alpha-arylalkanoic acids.

Starting in particular from compounds of formula II-A in the form of a single epimer, optically active compounds of formula I-A are obtained by rearrangement and hydrolysis.

One of the most important of these is naproxen, ie the S(+) enantiomer of 2-(6-methoxy-2-naphthyl)-propionic acid.

The following examples are described in order to better illustrate the present invention.

EXAMPLE 1

Preparation of a diastereoisomeric mixture of 2-[1-(chlorosulphonyloxy)-ethyl]-2-(5-chloro-6-methoxy-2-naphthyl)-4(R),5(R)-dimethoxycarbonyl-1,3-dioxolane Sulphuryl chloride (0.74 g; 5.5 mmoles) is slowly added under nitrogen to a mixture of 2-(1-hydroxyethyl)-2-(6-methoxy-2-naphthyl)-4(R),5(R)-dimethoxycarbonyl-1,3-dioxolane (1.1 g; 2.82 moles) in dimethylformamide (11 ml) and triethylamine (0.55 g; 5.5 mmoles) at −50° C.

After 6 hours, triethylamine (0.11 g; 1.1 mmoles) and sulphuryl chloride (0.15 g; 1.1 mmoles) are added, maintaining the temperature at −45° C. for a further 3 hours.

The reaction mixture is then poured into a 10% aqueous sodium bicarbonate solution and extracted with ethyl ether.

The organic phases are washed with 0.1N hydrochloric acid and then with water, dried with sodium sulphate and evaporated.

A residue is obtained (1.56 g) which is chromatographed in a column (silica gel; eluent: hexane/ethyl ether=6:4), to obtain 2-[1-(chlorosulphonyloxy)-ethyl]-2-(5-chloro-6-methoxy-2-naphthyl)-4(R),5(R)-dimethoxycarbonyl-1,3-dioxolane (1.03 g; yield 70%) as a mixture of the two diastereoisomers A and B.

$^1$H-NMR (90 MHz, CDCl$_3$-TMS), delta (ppm): 1.50 (3H, d, J=6 Hz); 3.40 (3H, s, diast.A); 3.53 (3H, s, diast.B); 3.83 (3H, s, diast.A+B); 4.00 (3H, s, diast.A+B); 5.00 (2H, q, Δv=30 Hz, diast.A+B); 5.26 (1H, q, J=6 Hz, diast.A); 5.23 (1H, q, J=6 Hz, diast.B); 7.10–8.26 (5H, aromatic).

EXAMPLE 2

Preparation of a diastereoisomeric mixture of the dimethyl ether of 2(R)-hydroxy-3(R)-[2-(5-chloro-6-methoxy-2-naphthyl)-propanoyl]-butanedioic acid A solution of 2-[1-(chlorosulphonyloxy)-ethyl]-2-(5-chloro-6-methoxy-2-naphthyl)-4(R),5(R)-dimethoxycarbonyl-1,3-dioxolane prepared as described in Example 1 (1,03 g; 1.97 mmoles in methanol (60 ml) and water (10 ml) is heated under agitation at 40° C. for 2 hours.

After evaporating the solvent under vacuum, the residue is suspended in ethyl ether, washed with a 5% sodium bicarbonate solution, then with water and then dried with sodium sulphate.

A residue is obtained (0.91 g) which is chromatographed in a column (silica gel; eluent: hexane/ethyl ether=4.6) to form the dimethylester of 2(R)-hydroxy-3(R)-[2-(5-chloro-6-methoxy-2-naphthyl)-propanoyl]-butanedioic acid (0.64 g; yield 77.7%) as a mixture of the two diastereoisomers A and B.

This mixture was crystallised from 1:1 hexane/ethyl ether to provide a mixture of the two diastereoisomers A and B (0.3 g) in the ratio of 75:25.

$^1$H-NMR (300 MHz, CDCl$_3$-TMS), delta (ppm):

Diastereoisomer A: 1.60 (3H, d, J=7 Hz); 3.16 (3H, s); 3.83 (3H, s); 4.03 (3H, s); 4.66 (1H, dd); 5.36 (1H, d, J=2.3 Hz); 7.27–8.19 (5H, aromatic).

Diastereoisomer B: 1.63 (3H, d, J=7 Hz); 3.60 (3H, s); 3.71 (3H, s); 4.03 (3H, s); 4.63 (1H, dd); 5.46 (1H, d, J=2.3 Hz); 7.27–8.19 (5H, aromatic).

EXAMPLE 3

Preparation of S(+)-2-[(5-chloro-6-methoxy)-2-naphthyl]-propionic acid

A solution of the two diastereoisomer esters A and B (0.28 g; 0.66 mmoles) prepared as described in Example 2 in a mixture of 1,4-dioxane (4.5 ml) and concentrated hydrochloric acid (4.5 ml) is heated under agitation to 90° C. for 1.5 hours.

The reaction mixture is cooled and extracted with ethyl ether, the organic phase being extracted with 5% sodium bicarbonate solution. The aqueous phases are acidified to pH 1 and extracted with ethyl ether.

2-[(5-chloro-6-methoxy)-2-naphthyl]-propionic acid is obtained (0.16 g; yield 92%). The ratio of the two enantiomers was determined by $^1$H-NMR using a shift reagent on the methyl ester, and by HPLC on the 2-octanoyl-ester, and was found to be 73:27.

$[\alpha]_D^{20} = +12°$ (c=0.5; CHCl$_3$)

$^1$H-NMR (300 MHz, CDCl$_3$-TMS), delta (ppm): methyl ester: 1.75 (3H, d, J=7 Hz); 3.84 (3H, s); 4.03 (1H, q, J=7 Hz); 4.19 (3H, s); 7.42–8.37 (5H, aromatic).

EXAMPLE 4

Preparation of S(+)-2-[(5-bromo-6-methoxy)-2-naphthyl]-propionic acid

2-[1-(S)-hydroxyethyl]-2-[(5-bromo-6-methoxy)-2-naphthyl]-4(R),5(R)-dimethoxycarbonyl-1,3-dioxolane is treated with sulphuryl chloride and triethylamine in accordance with the procedure described in Example 1.

2-[1-(S)-chlorosulphonyloxyethyl]-2-(5-bromo-6-methoxy-2-naphthyl)-4(R),5(R)-dimethoxycarbonyl-1,3-dioxolane is obtained and rearranged as described in Example 2 to the dimethyl ester of 2(R)-hydroxy-3(R)-[2-(5-bromo-6-methoxy-2-naphthyl)-propanoyl]-butanedioic acid.

This latter compound is subjected to acid hydrolysis in accordance with the procedure described in Example 3 to form S(+)-2-[(5-bromo-6-methoxy)-2-naphthyl]-propionic acid with $[\alpha]_D^{20} = +40°$ (c=0.5%, CHCl$_3$), optical purity 95%.

We claim:

1. A process for preparing alpha-arylalkanoic acids of formula

 (I)

in which
Ar represents a phenyl, diphenyl or naphthyl, possibly substituted with 1 or 2 groups chosen from C$_1$–C$_4$ alkyls, hydroxyls, halogens, alkoxys and haloalkoxys having 1–4 carbon atoms;
R represents a C$_1$–C$_4$ alkyl; comprising:
(a) reacting an alpha-hydroxyketal of formula

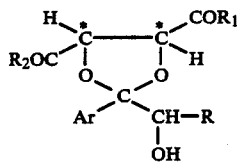 (V)

in which Ar and R have the aforesaid meanings; R$_1$ and R$_2$ can be the same or different and represent OR$_3$ groups in which R$_3$ represents a hydrogen atom, a C$_1$–C$_6$ alkyl, a C$_3$–C$_6$ cycloalkyl, a phenyl or benzyl, or an amino, monoalkylamino or dialkylamino group; and in which the carbon atoms marked with an asterisk both simultaneously have R or S configuration; with sulphur dioxide and halogen, or with a compound of formula

R$_4$X$_1$ (IV)

in which X$^1$ represents a chlorine atom or bromine atom; R$_4$ represents a POCl$_2$, PCl2, POBr$_2$, PBr$_2$, SeOCl or SeOBr group, an SOX or SO$_2$X group in which X represents a chlorine, fluorine or bromine atom, a trifluoromethyl group or an OR$_5$ group in which R$_5$ represents a C$_1$–C$_6$ alkyl, a phenyl or a tolyl; and in which the carbon atoms marked with an asterisk both simultaneously have R or S configuration; in an organic solvent, and possibly in the presence of a base, to prepare a compound of formula II

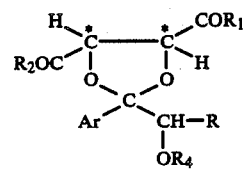 (II)

in which R, R$_1$, R$_2$, R$_4$ and Ar have the aforesaid meanings;
(b) rearranging a compound of formula II to obtain a compound of formula

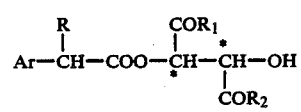 (III)

in which R, R$_1$, R$_2$ and Ar have the aforesaid meanings, in a protic solvent, possibly in mixture with water, or in a dipolar aprotic solvent, at a temperature of between ambient and the reflux temperature;
(c) hydrolysing a compound of formula III in an acid environment.

2. A process as claimed in claim 1, wherein in step (a) the base is used in a ratio of between 1:1.15 and 1:3 with respect to the alpha-hydroxyketal of formula V.

3. A process as claimed in claim 1, wherein in step (a) the compound of formula IV is used in a ratio of between 1:1.15 and 1:3 with respect to the alpha-hydroxyketal of formula V.

4. A process as claimed in claim 1, wherein in step (a) the base is chosen from pyridine, triethylamine and isopropylamine.

5. A process as claimed in claim 1, wherein in step (a) the compound IV is chosen from thionyl chloride, thionyl bromide, sulphuryl chloride, sulphuryl fluoride, trifluoromethanesulphonyl chloride and sulphuryl chloride fluoride.

6. A process as claimed in claim 1, wherein step (a) is carried out by reacting a compound of formula V with sulphur dioxide and chlorine.

7. A process as claimed in claim 1, wherein in step (a) the solvent is chosen from dimethylformamide, dimethylacetamide, hexamethylphosphorous triamide, tetramethylurea and dimethylthioformamide, or their mixtures with tetrahydrofuran or dichloromethane.

8. A process as claimed in claim 1, wherein in the step involving the rearrangement of ketals of formula II, the protic solvent is methanol or a methanol-water mixture.

9. A process as claimed in claim 1, wherein in the step involving the rearrangement of ketals of formula II, the dipolar aprotic solvent is dimethylformamide.

10. A process as claimed in claim 1 for preparing compounds of formula

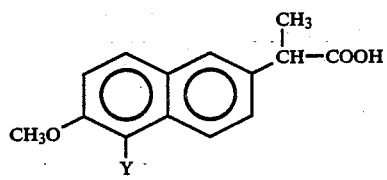 (I-A)

in which Y represents a hydrogen, chlorine or bromine atom, comprising the preparation and rearrangement of ketals of formula

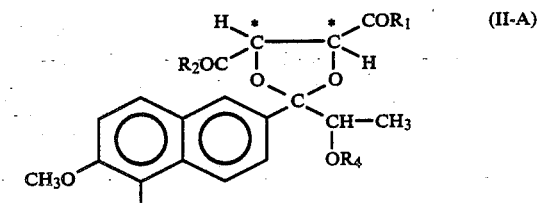 (II-A)

in which $R_1$, $R_2$ and $R_4$ have the meanings given in claim 1 and Y has the aforesaid meanings.

11. A process as claimed in claim 9 for preparing S(+)-2-(6-methoxy-2-naphthyl)-propionic acid, comprising the preparation and rearrangement of a ketal of formula II-A in which the carbon atom bonded to the $OR_4$ group has S configuration.

* * * * *